US010054580B2

(12) United States Patent
Wolf, Jr.

(10) Patent No.: US 10,054,580 B2
(45) Date of Patent: *Aug. 21, 2018

(54) SYSTEMS AND METHODS FOR AN EQUILIBRIUM WET BATH

(71) Applicant: Alcotek, Inc., St. Louis, MO (US)

(72) Inventor: Karl R. Wolf, Jr., Eureka, MO (US)

(73) Assignee: Alcotek, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/693,925

(22) Filed: Sep. 1, 2017

(65) Prior Publication Data

US 2017/0363611 A1 Dec. 21, 2017

Related U.S. Application Data

(63) Continuation of application No. 14/932,637, filed on Nov. 4, 2015, now Pat. No. 9,778,247.

(60) Provisional application No. 62/074,975, filed on Nov. 4, 2014.

(51) Int. Cl.
*G01N 33/497* (2006.01)
*G01N 33/00* (2006.01)

(52) U.S. Cl.
CPC ..... *G01N 33/4972* (2013.01); *G01N 33/0006* (2013.01)

(58) Field of Classification Search
CPC .................................................. G01N 33/4972
See application file for complete search history.

(56) References Cited

U.S. PATENT DOCUMENTS

| 3,817,451 | A | * | 6/1974 | Ramsey | F25B 49/027 236/49.3 |
|---|---|---|---|---|---|
| 3,854,319 | A | | 12/1974 | Burroughs et al. | |
| 7,934,577 | B2 | | 5/2011 | Walter et al. | |
| 8,191,435 | B2 | * | 6/2012 | Grate | G01N 1/2214 73/863.21 |
| 2011/0219780 | A1 | * | 9/2011 | Prabhu | F01K 13/00 60/775 |
| 2011/0226605 | A1 | * | 9/2011 | Thiers | B01D 1/305 203/10 |
| 2012/0196147 | A1 | | 8/2012 | Rabiei | |
| 2012/0210581 | A1 | * | 8/2012 | Wallaert | B22F 3/002 29/890.03 |
| 2014/0069137 | A1 | * | 3/2014 | Wu | F25B 1/00 62/498 |
| 2016/0107121 | A1 | | 4/2016 | Lienhard et al. | |

FOREIGN PATENT DOCUMENTS

| WO | 9714947 A2 | 4/1997 |
| WO | 2014003674 A1 | 1/2014 |
| WO | 2014164818 A1 | 10/2014 |

OTHER PUBLICATIONS

International Search Report, International Patent Application No. PCT/US2015/059043, dated Nov. 4, 2015, 9 pages.

* cited by examiner

*Primary Examiner* — Clayton E Laballe
*Assistant Examiner* — Dennis Hancock
(74) *Attorney, Agent, or Firm* — Lewis Rice LLC

(57) ABSTRACT

A wet standard calibration system which utilizes a heat conducting foam with the liquid therein to serve as a primary heating device to avoid the need to include mechanical agitation. The system is particularly useful for generating a vapor comprising water and ethanol which can be used for the calibration of breath alcohol testers.

6 Claims, 5 Drawing Sheets

SYSTEMS AND METHODS FOR AN EQUILIBRIUM WET BATH

CROSS REFERENCE TO RELATED APPLICATION(S)

This application is a Continuation of U.S. Utility patent application Ser. No. 14/932,637, filed Nov. 4, 2015, which claims the benefit of U.S. Provisional Application Ser. No. 62/074,975 filed Nov. 4, 2014. The entire disclosure of both the above documents is herein incorporated by reference.

BACKGROUND

1. Field of the Invention

This disclosure relates to the field of generation of solutes in equilibrium with their vapor phase. These are commonly used as wet bath calibration systems such as to calibrate breath alcohol testing equipment.

2. Description of the Related Art

For the purposes of public safety on the roads and elsewhere, there is a need to make sure that individuals are not operating potentially dangerous machines (such as automobiles) while they are impaired by the effects of alcohol consumption. To try and prevent people from driving drunk, most states have enacted laws that impose fines or other criminal penalties if individuals have a breath or blood alcohol level above a certain amount. In order to effectively enforce these laws, it is necessary to be able to measure the alcohol concentration in human breath (which is often used as an easy method for approximating blood alcohol if it is not used directly) and compare the results against legal limits. There are a variety of measuring instruments used for determining the concentration of alcohol in human breath ranging from small hand held devices to larger bench top units and machines built into cars or certain machinery. Since a determination of breath alcohol above the legal threshold can result in criminal penalties, loss of a job, or other sanctions, the accuracy of these instruments is paramount.

Great care and effort is taken by owners and managers of evidential breath testing equipment to ensure proper calibration as well as follow-up accuracy checks at generally regular intervals. In attempts to eliminate the labor time of this testing and concerns about human error in the testing, manufacturers of breath testing equipment often offer automated or semi-automated methods for doing calibrations and accuracy checks. Some users of breath alcohol test equipment, such as Motor Vehicle Law Enforcement, may even require an automatic accuracy check every time they test a human subject and sometimes even before and after the human subject test simply to make sure that the device is reading correctly and will supply court-admissible evidence.

There are generally different standards used when calibrating breath testers. As breath (containing alcohol or not) is a vapor comprising exhalation gases and vaporized substances and can be quite complex, instruments that measure alcohol concentration in breath vapor generally need standards to be provided in a similar form for accurate calibration. Calibration gases of many sorts are well known in many applications including breath testing. In breath testing, the calibration standards are generally of two types, wet and dry. Wet standards include water vapor; dry standards do not. Some argue that wet standards are better because they include moisture like human breath and are therefore more representative. Effectively, the argument is that the closer the calibration gas is to the actual constitution of an expected human breath at the tipping point of legal consequences, the more robust the calibration is, and the more likely that an evidentiary reading will be determined to be "correct" in the end. However, commercial providers of both wet and dry standards generally advertise +/−2% accuracy of calculations with actual breath.

In either case, the alcohol concentration of measurement interest is in a carrier gas such as air, breath, or nitrogen. A typical breath ethanol concentration which would result in illegal driving in most states is 200 parts per million (ppm) or more. That is 200 parts ethanol per million parts of carrier gas regardless of the carrier gas composition. Therefore, the standards generally provide samples that contain very close to 200 ppm to make sure the dividing line is correctly calibrated.

Wet standards have a long history in breath testing, are well accepted, and the liquids used in them can be certified by chemical analysis against National Institute of Standards and Technology (NIST) traceable standards. The standards are prepared by combining known amounts of ethanol and water in a partially filled jar that is accurately heated (generally to 34° C.) and then maintained at that temperature. These heated jars are sold commercially and are referred to as Simulators. At equilibrium, the quiescent headspace above the jar contains a vapor with a known concentration of ethanol along with nearly 100% relative humidity at that temperature. In one special case of a wet standard, known as an "Equilibrator," no heating is used, but the operator is required to read its temperature (usually equal to ambient) and follow a lookup table to see what gas concentration is delivered when similarly blown through as in a standard simulator.

By introducing sober human breath or air from another suitable source into the jar (by blowing or injecting gas into the liquid), the known concentration of ethanol vapor exits the headspace and can be introduced into a breath tester at which point a measurement may be taken. Typically, a liter or more of gas is blown through the simulator for each test. As newly introduced air or breath bubbles up through the liquid, it replaces the gas exiting the simulator with newly equilibrated gas.

Generally, the simulators of the prior art go to great lengths to keep the temperature of the system constant at 34° C.+/−0.1° C. This is because, as the temperature changes, so does the equilibrium point. Thus, the alcohol concentration in the gas varies with the temperature of the system. For example, at 34° C., a 0.1° change can represent well over a 0.5% change in the gas. Notably, this air/water equilibrium relationship for ethanol over temperature is not linear. Those skilled in the art will recognize, as shown in table 1 below that the ratio of ethanol concentration in the air to the water goes up in a non-linear fashion as the temperature goes up:

TABLE 1

| ° C. | $K_{A/W} \times 10^3$ |
| --- | --- |
| 1 | 0.035 |
| 5 | 0.046 |
| 10 | 0.073 |
| 15 | 0.107 |
| 20 | 0.155 |
| 25 | 0.217 |
| 30 | 0.310 |
| 35 | 0.418 |

TABLE 1-continued

| ° C. | $K_{A/W} \times 10^3$ |
|---|---|
| 37 | 0.470 |
| 40 | 0.562 |

Thus, while these types of wet calibration systems are well established in the art, there can be no question that there is some concern about their specific ability to provide a highly accurate sample in today's demanding environment for repeatable calibration and testing of measurement devices. Prior breath testing devices were commonly allowed a +/−10% accuracy in their readings. As the error introduced from the calibration sample was relatively small compared to this, it was of relatively little concern as most error would exist in the breath testing device itself. However, today's standards are much more rigorous and most breath testing instruments are allowed, at most, a +/−5% margin of error and are often allowed much less. These specifications can be extraordinarily hard to meet when a calibration standard can, by itself, introduce up to two-thirds of the allowable error. In effect, the breath testing devices are effectively allowed to have less variation than the standards they are tested against in order to pass.

While there are some arguments that this simply makes the resultant systems all the more accurate, it does make clear that even if all procedures for accurate calibration of the device are followed and the device is infinitely accurate, there has always been a degree of uncertainty in the accuracy of the gas used to calibrate the device. This high degree of uncertainty in the standard has become one of the biggest components in uncertainty in the instruments and has, in some respects, resulted in a barrier to the recognition that instruments may be even more accurate than they currently appear because they simply cannot be accurately calibrated. Thus, there is a need in the art for calibration systems which reduce their contribution in the uncertainty of the testing equipment and therefor allow for recognition as to the actual accuracy of the testing equipment itself.

SUMMARY

The following is a summary of the invention, which should provide to the reader a basic understanding of some aspects of the invention. This summary is not intended to identify critical elements of the invention or in any way to delineate the scope of the invention. The sole purpose of this summary is to present in simplified text some aspects of the invention as a prelude to the more detailed description presented below.

Because of the above and other problems in the art, described herein, among other things, is a wet standard calibration device which utilizes a heat conducting foam with the liquid therein to serve as a primary heating device to avoid the need to include mechanical agitation.

Described herein, among other things is a wet calibration system comprising: a vessel; a thermally conductive foam placed within said vessel so as to take up a portion of an internal volume of said vessel, a remaining portion of said volume not taken up by said foam comprising a headspace, said headspace including a gas; a liquid mixture: said liquid mixture including a solvent and a solute; and said liquid mixture being in thermal contact with said thermally conductive foam; and a heating element; wherein, said heating element heats said thermally conductive foam; wherein said thermally conductive foam heats said liquid mixture to a temperature; and wherein heating of said liquid mixture generates a vapor in said headspace, said vapor having a concentration of solute relative to said temperature.

In an embodiment of the wet calibration system, the thermally conductive foam is a reticulated foam.

In an embodiment of the wet calibration system, the thermally conductive foam is a metal foam.

In an embodiment of the wet calibration system, the thermally conductive foam is an aluminum foam.

In an embodiment of the wet calibration system, the thermally conductive foam is a copper foam.

In an embodiment of the wet calibration system, the liquid is not within said headspace.

In an embodiment of the wet calibration system, the liquid occupies less volume in said headspace than said foam occupies in said vessel.

In an embodiment of the wet calibration system, all the liquid is within one half (½) the distance of the size of an interstitial opening in said foam from a surface of said foam.

In an embodiment of the wet calibration system, the solute is ethanol and said solvent is water.

In an embodiment of the wet calibration system, the gas is air.

In an embodiment, the wet calibration system includes an exhaust vent.

In an embodiment of the wet calibration system, the exhaust vent is used to provide a vapor sample to a breath alcohol tester.

There is also described herein a wet calibration system comprising: a vessel; a thermally conductive foam placed within said vessel; a liquid mixture: said liquid mixture including a solvent and a solute having a known ratio; and said liquid mixture being in thermal contact with said thermally conductive foam; a heating element configured to heat said liquid mixture to a known temperature; a gas; and a vapor, said vapor also comprising said solvent and said solute; wherein, said vapor has a known concentration of said solute at equilibrium given said known temperature and; wherein said liquid and said vapor are in equilibrium.

In an embodiment of the wet calibration system, the thermally conductive foam is a reticulated foam.

In an embodiment of the wet calibration system, the thermally conductive foam is a metal foam.

In an embodiment of the wet calibration system, the thermally conductive foam is an aluminum foam.

In an embodiment of the wet calibration system, the thermally conductive foam is a copper foam.

There is also described herein a method of generating a vapor comprising: providing a vessel having a thermally conductive foam placed therein; placing a liquid mixture of a solvent and a solute in said vessel so as to at least partially submerge said foam in said liquid; heating said foam to generate a vapor from said liquid, said vapor also including said solvent and said solute and said vapor and said liquid being in equilibrium.

In an embodiment of the method, the thermally conductive foam is a metal foam.

In an embodiment of the method, the solvent is water and said solute is ethanol.

DETAILED DESCRIPTION OF THE PREFERRED EMBODIMENT(S)

Although the present invention will be described hereinafter with particular reference to the accompanying drawings, it is to be understood at the outset that it is contemplated that the present invention may be varied in specific detail from that illustrated and described herein while still achieving the desirable characteristics and features of the present invention. Further, while specific embodiments primarily designed to calibrate breath alcohol testers are depicted, it should be understood that components and features can be used across a variety of devices in different types of use. Accordingly, the description that follows is intended to be understood as a broad enabling disclosure directed to persons skilled in the applicable arts, and is not to be understood as being restrictive.

Figure 1:
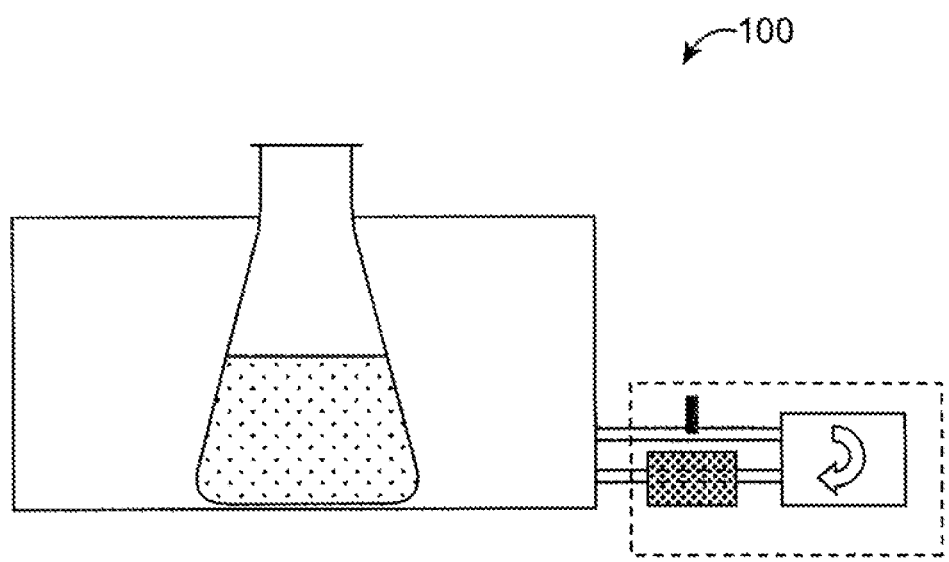
FIG. 1 shows an embodiment of a wet calibration device of the prior art that utilizes a circulating pump for agitation.
Figure 2A:
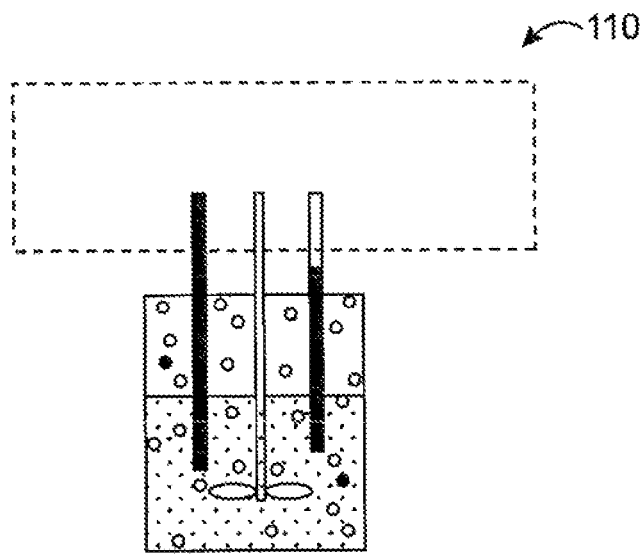
FIGS. 2A and 2B respectively show embodiments of a wet calibration device of the prior art that use a mechanical stirrer and a circulating pump for agitation.
Figure 2B:
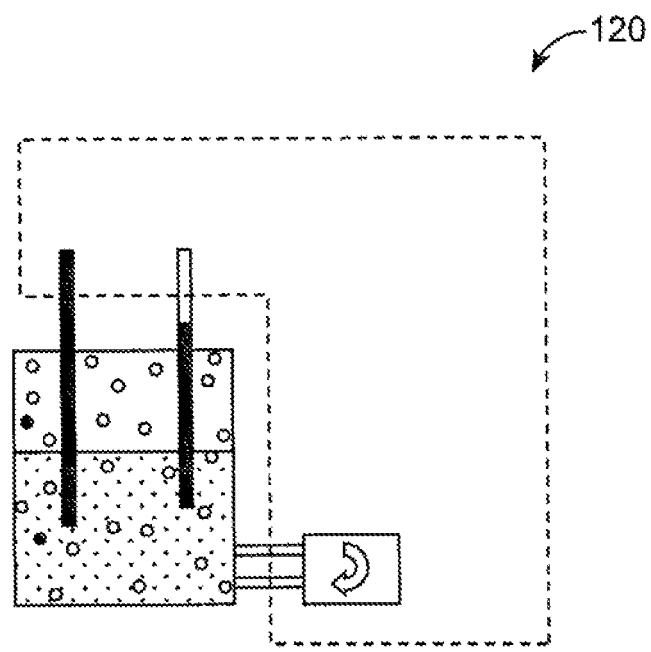

With regards to traditional wet calibration systems, such as those shown in FIG. 1, which provides a traditional water bath system (100), FIG. 2A, which provides a mechanically stirred water bath (110), and FIG. 2B which provides a circulating water bath (120), the concern is that the concentration of water and ethanol in the vapor is actually directly dependent on the temperature at the air/water (or more accurately gas/liquid) interface, and not the temperature in the water as a whole, which is often more conveniently and accurately measured and maintained. The temperature at the interface can be extremely difficult to measure precisely under ideal conditions and the need to include some form of mechanical agitation to make the liquid a more homogenous temperature can also result in this exact interface temperature being even more difficult to measure and, often more importantly, to maintain.

Figure 3:
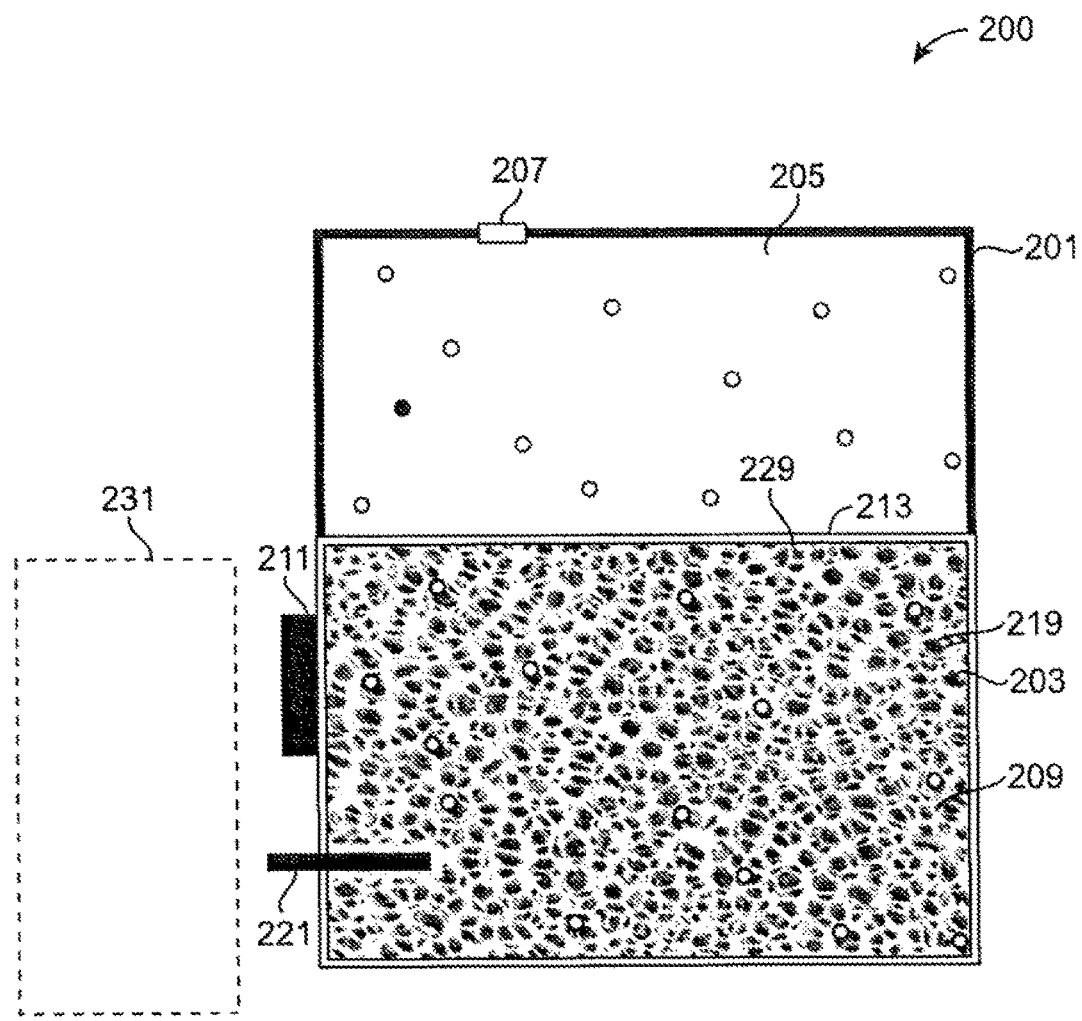
FIG. 3 shows an embodiment of a wet calibration device including a heat conductive foam within the liquid portion.
Figure 4:
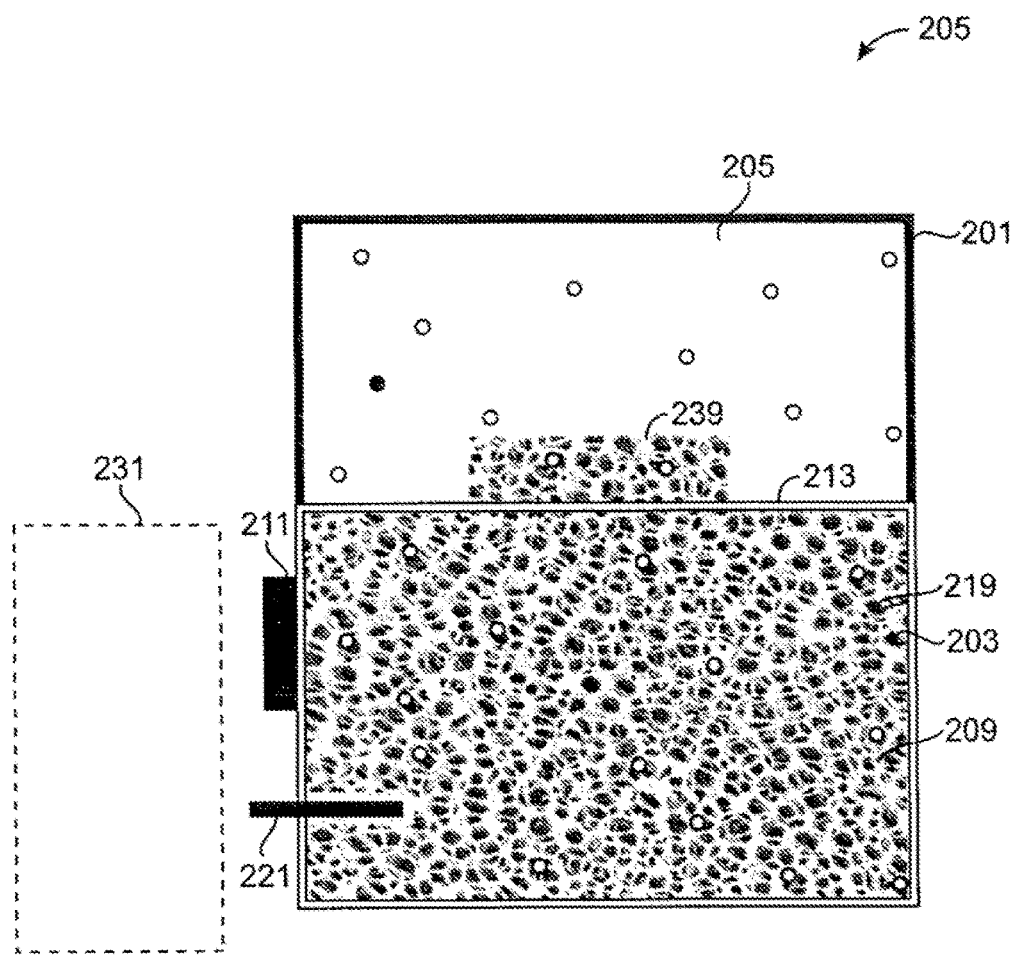
FIG. 4 provides an embodiment of a wet calibration device including a heat conductive foam that extends from the liquid portion into the gas space.
Figure 5:
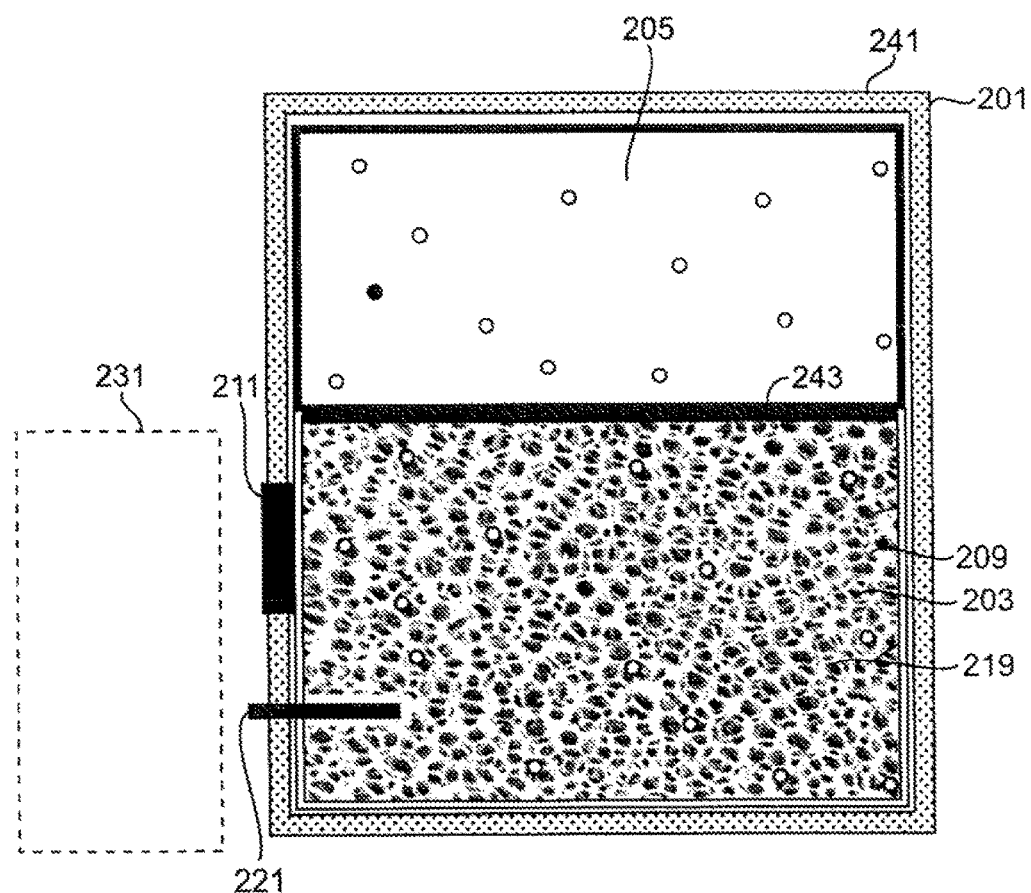
FIG. 5 provides an embodiment of a portable wet calibration device including a heat conductive foam and a vapor permeable membrane.

FIGS. 3, 4, and 5 provide for three embodiments of a wet calibration system which uses a heat conducting foam (209) in order to heat the liquid (203). The system (200) generally comprises a closed vessel (201) interior within which liquid (203) and vapor (205) can be held at a constant temperature. The vessel (201) may include a valve mechanism (207) or other structure to allow for vapor (205) from the system (200) to be dispensed to a device to be tested or calibrated and/or for pressure release. The valve mechanism (207) can also or alternatively act as a septum where an inlet from a gas analyzer (e.g. a breath straw, tube, or probe) can be inserted into the gas space for extraction of a sample into the analyzer. Alternatively, the vessel (201) may be designed to have necessary components of a device to be tested enclosed within itself to allow for a sealed environment.

It should be recognized herein that this disclosure will generally refer to the system (200) including a vapor (205) and a liquid (203). It should be recognized that these terms are used because, in desired equilibrium, some of the liquid (203) will generally be suspended in a gas (205) present in the system (200). In an embodiment for calibration of breath alcohol testing equipment, the liquid (203) will generally comprise a liquid solvent (generally water but that is not required) with a liquid solute (generally ethanol but that is not required) therein. The vapor (205) will generally comprise air (or a gas of roughly similar composition to air although that is not required) with vaporized liquid solute and solvent therein. However, the composition of the liquid (203) and vapor (205) used herein are not necessary and virtually any liquids, gases, or vapors can be included depending on the desired equilibrium state and the purpose to which the system (200) is to be put.

Because of the flexibility of terminology, it should be recognized that references herein to a "gas" may refer to a carrier gas (e.g. air) or may refer to the carrier gas and liquid vapor solution and may be used interchangeably with "vapor." Further, "liquid" may refer to a solvent, solute, or both in combination. Also a "fluid" will generally refer to the liquid, but may be used to refer to material in either the liquid or gas state and will often be used to indicate that material in either state is being indicated.

Heat is provided to the liquid (203) via a conducting reticulated foam (209), generally a metal foam, as the primary heating element. In an embodiment, the liquid (203) generally completely fills all the interstitial openings of the foam (209), keeping all portions of the liquid (203) in close contact with the foam (209) and at constant temperature. In such an embodiment, the liquid level (213) (and thus the line of liquid/gas interface (213)) will generally be very close to the height of the foam (209) so that the gas/liquid interface (213) is at or near the uppermost surface of the foam (209). In an embodiment, the interface (213) may begin just slightly above the foam (209) so as to provide an actual planar interface (213) between vapor (205) and liquid (203). In an alternative embodiment, the interface (213) level may be slightly below the upper surface of the foam (209) so as to provide for gas (205) heating as contemplated below in conjunction with FIG. 4.

The various interstitial openings (219) within the foam (209) are preferably fully interconnected (allowing liquid (203) at any point in the foam (209) to potentially flow to any other point in the foam (209)) and open to the outside of the foam (209) (e.g. an opening (219) would contact a wall of the vessel (201) so that liquid (203) could exit the foam (209) depending on the space between the wall of the vessel (201) and the outside of the foam (209)). However, this is not necessary in all embodiments. The interconnection, however, allows fluids to pass freely into and out of the foam (209) structure and inhibit the creation of heated "pockets" which cannot readily transfer heat.

The foam (209) may be of any type that is capable of being heated or of generating heat and transferring that heat to the liquid (203). Typically the foam (209) will be a metal foam and is preferably a material which does not react with water or ethanol. This can include, for example, copper, aluminum, silver, or gold One example of a useable reticulated foam (209) is Duocell® from ERG Aerospace Corporation. The foam (209) will generally be designed to be heat conductive even if it is non-metallic.

As shown in FIG. 3, the liquid (203) in the vessel (201) does not require circulation for precise temperature control as virtually all the liquid (203) is in very close proximity to the material of the foam (209) as it is within the channels (219) of the foam (209). In an embodiment, if the foam is manufactured with a generally consistent opening (219) size, the liquid will have a maximum distance from the foam of one-half (½) the opening size. Further, this distance can then also be used to dictate the preferred depth of liquid (203) above the upper surface of the foam (109). As the foam (209) transfers heat to the liquid (203), the liquid (203) will be efficiently heated by its proximity at a general regular rate.

Further, to the extent there are small temperature variations (which are believed to be slight due to the close proximity), temperature induced currents will generally cause warmer and cooler liquid (203) to be intermixed quickly and efficiently throughout the foam (209). Thus, temperature in all the liquid (203) which is within the foam (209) should be maintained at a very constant temperature without the use of or need for mechanical agitation.

Because the liquid (203) bath is not being mechanically agitated or mechanically circulated, the liquid (203) and liquid/vapor interface (213) represent a simpler system of temperature control while providing a liquid (203) bath with an essentially homogeneous or near homogenous temperature. The temperature of the liquid/gas interface (213) can, therefore, be more precisely controlled. Specifically, the temperature of any part of the liquid (203) will generally be very close to any other part and, to the extent they are different, they should rapidly converge by simple heat transfer and convection currents. Thus, the entirety of the liquid (203) is generally at a fairly constant and controlled temperature. Such consistency, means that the temperature of the liquid (203) at the liquid/gas interface (213) is also generally very close the temperature of all the other liquid (203) and since agitation and movement of the liquid (203) at the liquid/gas interface (213) is relatively minimal, its temperature is highly controllable.

While not required, it is preferred that the vessel (201) be thermally conductive to better facilitate the transfer of heat from a heater (211) which can be mounted outside the vessel (201) to the reticulated foam (209). Good thermal connectivity may be achieved by press fitting the outside shape of the foam (209) into the vessel (201), which is preferably also made of metal or other conducting material, so that the foam (209) is forced to have many good thermal contacts with and throughout the enclosure and by using an enclosure with a large amount of thermal conductivity. Heating elements (211) also can be distributed around the outside of the container to heat from a variety of different positions simultaneously. Regardless of the types of heating elements (211) used, it is generally preferred that the system (200) be capable of being heated and maintained at a specific temperature above ambient for a long period of time to further promote a consistent temperature. External heating, however, is not required and in an alternative embodiment the heating element (211) may be mounted interior to the vessel (201) or the foam (209) itself may convert another form of input (for example, an electrical signal) into heat directly to heat the liquid (203).

It is generally preferred that in order to monitor and maintain the temperature inside the vessel (201) that there be provided a thermometer (221) arranged to detect the temperature inside the vessel (201). The thermometer (221) also may be conductive, and may obtain the temperature from the exterior surface of the vessel (201). However, the thermometer (221) may operate best if it is within the vessel (200). As such, it may be positioned in the liquid (203), in the vapor (205), or at the gas/liquid interface (213). It is generally believed that more accurate temperature control can be achieved if the thermometer (221) is in contact with the liquid (203) only and is positioned within a well deep inside the foam (209) but at a point where liquid (203) is capable of flowing to the other points in the foam (209) and particularly to the liquid/gas interface (213). In this way, the thermometer (221) is measuring the temperature of the liquid at a point where thermal currents should have reached an equilibrium. In alternative embodiments, the thermometer may be in contact with the foam (209), gas (205), and/or interface (213) as well as the liquid (203).

The thermometer (221) can be any of a variety of temperature sensors such as thermistors or thermocouples. Generally, the type of thermometer (221) will depend on the exact nature of an associated control system (231). The control system (231) would serve to interconnect the output of the thermometer (221) to control of the heater (211) such that when the thermometer (221) is to detect a change in temperature, the output of the heater (211) would be automatically adjusted to compensate in a feedback loop type of arrangement. Such arrangements are well known to those of ordinary skill in the art and therefore not discussed in detail here. To improve control, the thermometer (221) will generally be located in a position that delivers the best indication that the fluid in the vessel (200) has reached equilibrium (e.g. it may be at a point where equilibrium takes longer to obtain) and be calibrated so that the temperature detected can be readily converted into the temperature at the gas/liquid interface (213) that is desired.

Because the vessel (201) is designed generally to be sealed, and may be operating for a period of time without being used for any testing of external devices (which would necessarily vent some vapor), the gas space (205) may include one or more venting valves (which may be the measurement valve (207) or another valve) to maintain pressure inside the vessel (201) in equilibrium with ambient pressure and inhibit any potential danger to the vessel (201) from a severe over or under pressure. Further, use of valves to maintain pressure will also assist in maintaining the temperature internal to the vessel (201) as the temperature will not be affected by changes in pressure as it internally heats or cools. The system may also include a liquid input which can server to add additional liquid (203) to the vessel (201) as the amount decreases. This can provide that the liquid (203) level does not get below a certain desired level to also assist in maintaining equilibrium.

It should be recognized that while the above description contemplates the foam (209) being used to heat the liquid (203) above ambient, this is by no means required. In an embodiment, the foam (209) with attached heater (211) may be used to heat the liquid (203) above ambient temperature, or the foam (209) may be used to cool the liquid (203) below ambient temperature by use of a connected thermoelectric element based on the Peltier effect, for example. The system (200) also can be used without the heater (211) as contemplated later herein.

FIG. 4 provides for an alternative embodiment of the system (200) where the reticulated foam (209) has a portion (239) which extends into the gas (205) space. As shown in FIG. 4, the extension (239) will generally not pass through the entire plane of the liquid/gas interface (213), but will instead only extend at a sub-portion. However, in an alternative embodiment, the foam (209) may extend at all points placing the plane of interface (213) within the foam (209). An embodiment with the foam (209) extending into the gas space (205) can provide for additional temperature control of the entire system (200). Specifically, as the portion of the foam (239) in the gas space (205) is filled with gas (205) and is contiguous with the foam (209) in the liquid space (203), this creates a continuous heat exchanger across the interface (213), a portion of which heats the liquid (203) and a portion of which heats the gas (205). Like the liquid (203), the gas (205) can pass freely into and out of the foam structure (239). However, the heat can now exchange directly with either the liquid (203) and/or the gas (205) from the foam (239) or (209). This can provide for a better fluid flow within the vessel (201).

As is shown in FIG. 5, a vapor permeable membrane (243) may be used to keep liquid (203) from ever entering the gas space (205). While in most cases such interaction is not a problem so long as it is minimal (e.g. in the form of a popping bubble), prevention of the interaction can be important in a device (200) where orientation cannot be controlled at all times. For example, if the device (200) is used in a portable application, the device (200) may be positioned on a surface which may not be level. This could cause the upper most foam surface (229) to cross the liquid/gas threshold (213) at an angle and in a manner that may not allow for accurate heating. Similarly, as seen in FIG. 5, part or all of the system (200) also may be thermally insulated (241) for better temperature control of the entire system (200) or parts thereof where such insulation (241) is desired.

While the system will generally be used to provide for the ability to specify and hold a particular temperature in the liquid (203) (and at the gas/liquid interface (213)) so as to provide for a consistent, repeatable, steady state inside the chamber (200) without the need for mechanical agitation, it should be recognized that the system (200) can provide for a variety of potential uses and operations within that realm.

In the first instance, the system (200) can be used to create a known vapor (205) mixture with a high degree of accuracy. With a partition relationship between a solute in a liquid phase (203) (in a solvent) and said solute in a gaseous phase (205) (in equilibrium above the liquid) known at a given temperature, by mixing the solute in some exact concentration of solvent (which is relatively easy), and placing the proper amount of such liquid mix (203) in the vessel (201), a vapor (205) of predictable concentration is created in the headspace above. Such vapor (205) can be used for any variety of purposes including calibration of gas analysis equipment or in producing vapors (205) of known concentration to have certain effects (e.g. for vapor etching, theatrical vapor effects, or for precise steam cooking). By varying the liquid (203) concentration at will, proportional concentrations of gas may be created at will.

It should be recognized in the above, that while making a specific vapor (205) from a specific liquid (203) by having a fixed temperature is generally contemplated, it is generally the case that temperature variation can be used to create different concentrations from the same source liquid (203). Thus, with a single liquid (203) mix of known concentration of solute in solvent, the temperature of the liquid (203) can be controlled at will, with precision, to create an accordingly proportional and predictable vapor (205) concentration. This can be used for variations of the vapor (205) concentration over time, or to allow the device (200) to provide a wide variety of vapor (205) concentrations depending on application.

Further, while the above generally presumes that the temperature is controlled by the device (200), in some cases the device (200) can actually be used to predict potential errors produced by ambient conditions. For example, in the event that the device (200) is being used in an unknown environment, the heater (211) can be turned off and the system (200) can be used to measure the temperature at ambient. From this, and knowledge of the concentration of the liquid (203) mix, the system (200) can determine the vapor (205) concentration at ambient. Within some reasonable ambient temperature range, the range of vapor (205) concentrations produced may still be within a reasonable enough range to calibrate or check gas analysis equipment, even though the user must use the vapor (205) concentration predicted by the ambient temperature and the system (200) instead of being able to always count on a specific concentration. Thus, even though the exact concentration of the vapor (205) is not under absolute control of the user, it is still a precise enough value to use. Further, because the system (200) can create a known calibration vapor (205) at ambient temperature, a remote device can be correctly calibrated at ambient. In this way, a device being calibrated where the reaction for measurement is temperature dependent (e.g. not the same across all temperatures) can be calculated at its current ambient temperature, resulting in the most accurate calibration possible.

Still further, the device (200) also can be used to evaluate a liquid (203) mix of unknown concentration of a known solute. Specifically, by placing the liquid (203) mix at a specific temperature (or across a variety of temperatures), the headspace may be drawn off and analyzed by a previously calibrated gas analyzer. Based on the calculated amount of material in the gas and the temperature, the gas concentration may now be used to determine the concentration of the solute in the liquid (203) mix. For example, this technique could be used to measure the concentration of ethanol in alcoholic beverages using only a traditional breath analyzer. This could be useful, for example, in a traffic stop where a law enforcement officer may suspect that a beverage container includes an alcoholic beverage, but requires some level of proof on site.

While the inventions have been disclosed in connection with certain preferred embodiments, this should not be taken as a limitation to all of the provided details of any invention. Modifications and variations of the described embodiments may be made without departing from the spirit and scope of any invention herein disclosed, and other embodiments should be understood to be encompassed in the present disclosure as would be understood by those of ordinary skill in the art.

The invention claimed is:

1. A system for generating a vapor, the system comprising:
   a vessel having a thermally conductive foam placed therein;
   a liquid mixture of a solvent and a solute in said vessel so as to at least partially submerge said foam in said liquid;
   means for heating said foam to generate a vapor from said liquid, said vapor also including said solvent and said solute and said vapor and said liquid being in equilibrium.

2. The system of claim 1 wherein said thermally conductive foam is a metal foam.

3. The system of claim 1 wherein said solvent is water and said solute is ethanol.

4. The system of claim 1 further comprising:
   means for detecting a temperature of said liquid mixture.

5. The system of claim 4 wherein said means for detecting said temperature is external said vessel.

6. The system of claim 4 wherein said means for detecting said temperature is internal said vessel.

* * * * *